(12) United States Patent
Qiu et al.

(10) Patent No.: US 12,351,626 B2
(45) Date of Patent: Jul. 8, 2025

(54) ANTI-HUMAN INTERLEUKIN-33 MONOCLONAL ANTIBODY AND USE THEREOF

(71) Applicant: QYUNS THERAPEUTICS CO., LTD., Jiangsu (CN)

(72) Inventors: Jiwan Qiu, Jiangsu (CN); Wei Chen, Jiangsu (CN); Yong Kong, Jiangsu (CN); Huaiyao Qiao, Jiangsu (CN); Yiliang Wu, Jiangsu (CN); Tao Chen, Jiangsu (CN); Meijuan Wu, Jiangsu (CN)

(73) Assignee: QYUNS THERAPEUTICS CO., LTD., Jiangsu (CN)

( * ) Notice: Subject to any disclaimer, the term of this patent is extended or adjusted under 35 U.S.C. 154(b) by 0 days.

(21) Appl. No.: 18/593,108

(22) Filed: Mar. 1, 2024

(65) Prior Publication Data
US 2024/0309081 A1  Sep. 19, 2024

Related U.S. Application Data

(63) Continuation of application No. PCT/CN2021/136755, filed on Dec. 9, 2021.

(30) Foreign Application Priority Data

Sep. 3, 2021 (CN) .......................... 202111031678.2

(51) Int. Cl.
*C07K 16/24* (2006.01)
*A61K 39/395* (2006.01)

(52) U.S. Cl.
CPC ........ *C07K 16/244* (2013.01); *A61K 39/3955* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 2014/0271658 A1 | 9/2014 | Murphy et al. |
| 2016/0289322 A1 | 10/2016 | Fujino et al. |
| 2020/0048340 A1 | 2/2020 | Benschop et al. |

FOREIGN PATENT DOCUMENTS

| CN | 105051063 | 11/2015 | |
| CN | 109415436 | 3/2019 | |
| CN | 111620948 | 9/2020 | |
| CN | 112480252 | 3/2021 | |
| CN | 112979802 | 6/2021 | |
| CN | 113234157 | 8/2021 | |
| CN | 113272448 | 8/2021 | |
| CN | 113573733 | 10/2021 | |
| CN | 113603775 | 11/2021 | |
| EP | 3 088 517 | 11/2016 | |
| EP | 3 851 121 | 7/2021 | |
| WO | 2014/164959 | 10/2014 | |
| WO | 2017/187307 | 11/2017 | |
| WO | 2020/005487 | 1/2020 | |
| WO | 2020/054871 | 3/2020 | |
| WO | 2020/061571 | 3/2020 | |
| WO | 2020/097607 | 5/2020 | |
| WO | 2020/191270 | 9/2020 | |
| WO | WO-2023029280 A1 * | 3/2023 | ................ A61P 1/00 |

OTHER PUBLICATIONS

International Search Report issued May 17, 2022 in International Application No. PCT/CN2021/136755.
Catalan-Dibene, J. et al., "Interleukin 30 to Interleukin 40", Journal of Interferon & Cytokine Research, 2018, vol. 38, No. 10, pp. 423-439.
Kim, E., et al., "Development of an interleukin (IL)-33 sandwich ELISA kit specific for mature IL-33", Journal of Immunoassay and Immunochemistry, 2016; vol. 37, No. 6, pp. 585-596.
Okragly, A. J., et al., "Generation and Characterization of Torudokimab (LY3375880): A Monoclonal Antibody That Neutralizes Interleukin-33", Journal of Inflammation Research, Aug. 2021, vol. 14, pp. 3823-3835.
Li, Shu, et al., "Pretreatment with interleukin-33 reduces warm hepatic ischemia/reperfusion injury in mice", Chinese Medical Journal, 2013, vol. 126, Issue 10, pp. 1855-1859.
Lu, Dai, et al., "Designing Ligands of Antibody Affinity Chromatography Based on Molecular Dynamics Simulation and testing the binding ability of them", China Doctor Dissertation Full-text Database, 2016, Issue 3, pp. 1-105 (abstract in English).
Extended European Search Report issued Jan. 27, 2025, is corresponding European Application No. 21955808.7.
Ogg, G., "Proof-of-Concept Phase-2a Clinical Trial of ANB020 (Anti-IL-33 Antibody) in the Treatment of Moderate-to-Severe Adult Atopic Dermatitis", May 29, 2018, XP055540607, 11 pages.

* cited by examiner

*Primary Examiner* — Marianne P Allen
(74) *Attorney, Agent, or Firm* — Wenderoth, Lind & Ponack, L.L.P.

(57) ABSTRACT

Provided in the present application are an anti-human interleukin-33 monoclonal antibody and the use thereof. The monoclonal antibody has a high affinity for human interleukin-33, has neutralizing activity, and can be used for preventing or treating related diseases mediated by human interleukin-33.

7 Claims, 4 Drawing Sheets
Specification includes a Sequence Listing.

ANTI-HUMAN INTERLEUKIN-33 MONOCLONAL ANTIBODY AND USE THEREOF

REFERENCE TO AN ELECTRONIC SEQUENCE LISTING

The contents of the electronic sequence listing (Attach-B_Sequence_Listing-0125A.xml; Size: 15,655 bytes; and Date of Creation: Jun. 7, 2024) is herein incorporated by reference in its entirety.

FIELD OF THE INVENTION

The present application relates to the technical field of antibody drugs. Specifically, the present application relates to an anti-human interleukin-33 (hIL-33) monoclonal antibody and use thereof.

BACKGROUND OF THE INVENTION

Interleukin 33 (IL-33) is a key member of the IL-1 family, expressed in a variety of cells, such as epithelial cells, fibroblasts, endothelial cells, smooth muscle cells, macrophages and dendritic cells, etc.; due to IL-33 gene does not comprise a signal peptide, so it cannot be secreted and expressed, while when cells or tissues are damaged, it is released as an alarmin, which sends an alarm to immune cells expressing IL-33 receptors, and plays an important role in host defense, immune regulation and inflammation (Cayrol C. et al. (2014) Curr. Opin. Immunol. 31C:31-37; Liew F. Y. et al. (2016) Nat. Rev. Immunol. 16:676-689).

IL-33 receptor is a heterodimer molecule composed of ST2 (also known as ILIRL1) and IL-IR accessory protein (IL-1RAcP). ST2 is the receptor for IL-33 binding, and IL-1RAcP is a shared component of the receptors for IL-1α, IL-1β, IL-1F6, IL1F8, and IL1F9, not required for binding, but critical for signal transduction (Schmitz J. et al., (2005) Immunity. 23:479-490). Upon binding of IL-33 to ST2, IL-1RAcP is recruited to form an IL-33/ST2/IL1RAcP ternary complex, which subsequently induces signal transduction through the MyD88 adapter, IRAK1 and IRAK4 kinases, and TRAF6, ultimately activating MAPK and NFκB transcription factors (Cayrol C. et al., (2018) Immunol Rev., 281(1):154-168).

IL-33 has been proved to be associated with inflammatory diseases, and it acts on ST2-expressing immune cells, such as Th2 cells, eosinophils, mast cells, etc., to drive the production of type 2 immune cytokines, especially IL-5 and IL-13, thus triggering serious pathological changes in mucosal organs (Molofsky A. et al., (2015) Immunity. 42:1005-1019; Mjosberg J. M. et al., (2011) Nat. Immunol. 12:1055-1062). Inflammatory diseases related to IL-33 comprise atopic dermatitis, asthma, chronic obstructive pulmonary disease, etc. (Savinko T. et al., (2012) J. Invest. Dermatol. 132:1392-1400; Prefontaine D. et al., (2010) J. Allergy. Clin. Immunol. 125:752-754; Byers D. et al. (2013) J. Clin. Invest. 123:3967-3982).

The monoclonal antibody drug (Itepekimab/REGN3500) targeting interleukin-33 jointly developed by Regeneron and Sanofi is intended for the treatment of chronic obstructive pulmonary disease (clinical phase III), asthma (clinical phase II) and other inflammatory diseases. Etokimab/ANB020 developed by AnaptysBio is intended for the treatment of asthma, chronic sinusitis (clinical phase II) and other diseases.

SUMMARY OF THE INVENTION

The purpose of the present application is to provide a new anti-human interleukin 33 (hIL-33) monoclonal antibody, a pharmaceutical composition comprising the monoclonal antibody and a pharmaceutical use of the monoclonal antibody.

The specific technical solutions of the present application are as follows:

1. An isolated anti-human interleukin-33 monoclonal antibody, comprising three heavy chain complementarity determining regions and three light chain complementarity determining regions, and the three heavy chain complementarity determining regions are CDR-H1, CDR-H2 and CDR-H3, the three light chain complementarity determining regions are CDR-L1, CDR-L2 and CDR-L3, wherein:
   the amino acid sequence of CDR-H1 (in this specification, CDR-H1 represents heavy chain CDR1) is represented by SEQ ID NO: 1 (SYHMI);
   the amino acid sequence of CDR-H2 (in this specification, CDR-H2 represents heavy chain CDR2) is represented by SEQ ID NO: 2 (VIYPNSNIYYATWAKG);
   the amino acid sequence of CDR-H3 (in this specification, CDR-H3 represents heavy chain CDR3) is represented by SEQ ID NO: 3 (TIYVHVYSALSI);
   the amino acid sequence of CDR-L1 (in this specification, CDR-L1 represents light chain CDR1) is represented by SEQ ID NO: 4 (QASESVLNEVS);
   the amino acid sequence of CDR-L2 (in this specification, CDR-L2 represents light chain CDR2) is represented by SEQ ID NO: 5 (FASKLAS);
   the amino acid sequence of CDR-L3 (in this specification, CDR-L3 represents light chain CDR3) is represented by SEQ ID NO: 6 (QQDWSMDNIDNA).

2. The monoclonal antibody according to item 1, which comprises a heavy chain variable region and a light chain variable region, wherein
   the amino acid sequence of the heavy chain variable region is represented by SEQ ID NO: 7

(EVQLVESGGGLVQPGGSLRLSCAASGFSLSSYHMIWVRQAPGKGLEWV
GVIYPNSNIYYATWAKGRFTISRDNSKNTLYLQMNSLRAEDTAVYYCAR
TIYVHVYSALSIWGQGTLVTVSS);

the amino acid sequence of the light chain variable region is represented by SEQ ID NO: 8

(AFQMTQSPSSVSASVGDRVTITCQASESVLNEVSWYQQKPGKAPKLLI
YFASKLASGVPSRFSGSGSGTDFTLTISSLQPEDFATYYCQQDWSMDNI
DNAFGGGTKVEIK).

3. An isolated nucleic acid, encoding the monoclonal antibody of item 1 or 2.

4. A host cell, comprising the nucleic acid of item 3;
   the nucleic acid can be present on a vector; the vector can be of any type, e.g., a recombinant vector such as an expression vector; any of a variety of host cells can be used; in one embodiment, the host cell is a prokaryotic cell, e.g., E. coli. In another embodiment, the host cell is a eukaryotic cell, e.g., a mammalian cell, such as a Chinese Hamster Ovary (CHO) cell.

5. A method for producing a monoclonal antibody, comprising culturing the host cell of item 4 to produce the monoclonal antibody of item 1 or 2;

the method comprises expressing a recombinant vector encoding the anti-human interleukin-33 (IL-33) monoclonal antibody in a suitable host cell, thereby producing the monoclonal antibody; in some embodiments, the method comprises culturing a host cell comprising the nucleic acid encoding the anti-human interleukin-33 (IL-33) monoclonal antibody, thereby expressing the nucleic acid; the method can further comprise recovering the anti-human interleukin-33 (IL-33) monoclonal antibody from the host cell culture or host cell culture medium.

6. A pharmaceutical composition, comprising the monoclonal antibody of item 1 or 2 and a pharmaceutically acceptable carrier;

the pharmaceutical composition can further comprise an additional therapeutic agent (e.g., different anti-human interleukin-33 (IL-33) antibodies).

7. The pharmaceutical composition according to item 6, which is used for treating a disease related to human interleukin-33-mediated signal transduction.

8. The pharmaceutical composition according to item 7, wherein the disease related to human interleukin-33-mediated signal transduction is any one or two or more diseases selected from the group consisting of: asthma, chronic obstructive pulmonary disease (COPD), age-related macular degeneration (AMD), chronic sinusitis, atopic dermatitis, multiple sclerosis, arthritis, and inflammatory bowel disease.

9. Use of the monoclonal antibody of item 1 or 2 in the preparation of a medicament for treatment of a disease related to human interleukin-33-mediated signal transduction.

10. The use according to item 9, wherein the disease related to human interleukin-33-mediated signal transduction is any one or two or more diseases selected from the group consisting of: asthma, chronic obstructive pulmonary disease (COPD), age-related macular degeneration (AMD), chronic sinusitis, atopic dermatitis, multiple sclerosis, arthritis, and inflammatory bowel disease.

11. A method for treating a disease related to human interleukin-33-mediated signal transduction, which comprises administering the monoclonal antibody or the pharmaceutical composition of any one of the preceding items to a subject in need thereof.

12. The method according to item 11, wherein the disease related to human interleukin-33-mediated signal transduction is any one or two or more diseases selected from the group consisting of: asthma, chronic obstructive pulmonary disease (COPD), age-related macular degeneration (AMD), chronic sinusitis, atopic dermatitis, multiple sclerosis, arthritis, and inflammatory bowel disease.

The Effect of the Invention

The present application provides a novel anti-human interleukin-33 (IL-33) monoclonal antibody, which has comparable affinity for binding to human interleukin-33 compared with the existing anti-human interleukin-33 (IL-33) monoclonal antibody (Etokimab/ANB020), and its neutralizing activity at the cellular level is comparable to that of Etokimab/ANB020.

The monoclonal antibody drug (Itepekimab/REGN3500) targeting interleukin-33 developed by Sanofi is intended for the treatment of chronic obstructive pulmonary disease (clinical phase III), asthma (clinical phase II) and other inflammatory diseases, Etokimab/ANB020 developed by AnaptysBio for chronic sinusitis (clinical phase II).

The monoclonal antibody of the present application shows neutralizing activity comparable to that of Etokimab/ANB020 (expressed and prepared according to the sequences disclosed in a patent) at the cellular level, and it is expected to show good clinical effects in the prevention and treatment of related diseases.

DETAIL DESCRIPTION OF THE INVENTION

The scientific and technological terms mentioned in this specification have the same meaning as those generally understood by those skilled in the art. In case of any conflict, the definitions in this specification shall prevail.

In general, the terms used in this specification have the following meanings.

In this specification, "isolated" antibody is an antibody that has been separated from components of its natural environment. In certain embodiments, antibodies are purified to a purity greater than 95% or 99%, which is determined by, for example, electrophoresis (e.g., SDS-PAGE isoelectric focusing (IEF), capillary electrophoresis) or chromatography (e.g., ion exchange or reverse-phase HPLC). For a review of methods for assessing antibody purity, see, e.g., Flatman et al., J. Chromatogr. B848:79-87 (2007).

In this specification, "monoclonal antibody" means an antibody obtained from a population of substantially homogeneous antibodies, i.e., individual antibodies constituting the population are identical and/or bind the same epitope, except for possible variant antibodies (e.g., comprising naturally occurring mutations or arising during the production of monoclonal antibody products), such variants typically exist in trace amounts. Unlike polyclonal antibody products that typically comprise different antibodies directed against different determinants (epitopes), each monoclonal antibody of the monoclonal antibody products is directed against a single determinant on the antigen. Thus, the modifier "monoclonal" indicates the characteristics that the antibody is obtained from a substantially homogeneous population of antibodies and should not be construed as requiring that the antibody be produced by any particular method. For example, the monoclonal antibody to be used according to the present application can be prepared by a variety of techniques including, but not limited to, a hybridoma method, a recombinant DNA method, a phage display method, and a method using transgenic animals comprising all or part of the human immunoglobulin locus, such methods and other exemplary methods for preparing monoclonal antibodies are described herein.

In this specification, "affinity" means the strength of the sum of non-covalent interactions between a single binding site of a molecule (e.g., antibody) and its binding partner (e.g., antigen). As used herein, unless otherwise indicated, "binding affinity" means an intrinsic binding affinity that reflects a 1:1 interaction between members of a binding pair (e.g., antibody and antigen). The affinity of a molecule X for its partner Y can usually be denoted by the equilibrium dissociation constant ($K_D$). Affinity can be measured by common methods known in the art.

In this specification, human interleukin-33 (hIL-33) means that hIL-33 located in the nucleus is hydrolyzed by protease to form mature hIL-33, which is secreted to the outside of the cell and exerts the biological activity of hIL-33, and its amino acid sequence is represented by SEQ ID NO:9.

SEQ ID NO: 9:
SITGISPITEYLASLSTYNDQSITFALEDESYEIYVEDLKKDEKKDKVLL

SYYESQHPSNESGDGVDGKMLMVTLSPTKDFWLHANNKEHSVELHKCEKP

LPDQAFFVLHNMHSNCVSFECKTDPGVFIGVKDNHLALIKVDSSENLCTE

NILFKLSET

In this specification, "anti-human interleukin-33 (hIL-33) monoclonal antibody" means a monoclonal antibody capable of binding human interleukin-33 with sufficient affinity such that the monoclonal antibody can be used as a diagnostic and/or therapeutic agent targeting human interleukin-33.

The anti-human interleukin-33 monoclonal antibody of the present application does not bind to a target irrelevant protein. Herein, "irrelevant protein" refers to other proteins except the target human interleukin-33; herein, "not bind to . . ." refers to: in the case where the binding ability of the anti-human interleukin-33 (hIL-33) monoclonal antibody in the present application to the target human interleukin-33 is 100%, the binding ability of the anti-human interleukin-33 (hIL-33) monoclonal antibody in the present application to the irrelevant protein is less than 10%, such as 9%, 8%, 7%, 6%, 5%, 4%, 3%, 2%, 1%, or 0.

The anti-human interleukin-33 (hIL-33) monoclonal antibody of the present application can bind to interleukin-33 of humans and cynomolgus monkeys, but may not bind to interleukin-33 of other animal species. Herein, "other animal species" refers to animal species other than humans and cynomolgus monkeys, such as pigs, dogs, rabbits, rats, mice, guinea pigs, etc.; herein, when determining the species specificity of the anti-human interleukin-33 (hIL-33) monoclonal antibody in the present application, "not bind to . . ." means: in the case where the binding ability of the anti-human interleukin-33 (hIL-33) monoclonal antibody in the present application to the target human interleukin-33 is 100%, the binding ability of the anti-human interleukin-33 (hIL-33) monoclonal antibody in the present application to other animal species is less than 5%, such as 4%, 3%, 2%, 1%, or 0.

The anti-human interleukin-33 monoclonal antibody of the present application has an equilibrium dissociation constant ($K_D$) of ≤1 μM, ≤100 nM, ≤50 nM, or ≤40 nM.

Experimental results show that the anti-human interleukin-33 (hIL-33) monoclonal antibody of the present application can specifically bind to human interleukin-33 (hIL-33).

The anti-human interleukin-33 (hIL-33) monoclonal antibody of the present application is comparable to or superior to similar monoclonal antibody products on the market in terms of many biological activities. The biological activities include, for example, the activity of neutralizing NF-κB/AP-1 signal transduction in cells induced by recombinant/natural human interleukin-33, the activity of neutralizing the release of IL-5 from KU812 cells induced by interleukin-33, the activity of neutralizing the release of IFN-γ from human whole blood induced by interleukin-33, and so on.

In one embodiment, the amino acid sequence of the heavy chain of the anti-human interleukin-33 (hIL-33) monoclonal antibody of the present application is represented by SEQ ID NO: 10; the amino acid sequence of the light chain is represented by SEQ ID NO: 11.

SEQ ID NO: 10
EVQLVESGGGLVQPGGSLRLSCAASGFSLSSYHMIWVRQAPGKGLEWVGV

IYPNSNIYYATWAKGRFTISRDNSKNTLYLQMNSLRAEDTAVYYCARTIY

VHVYSALSIWGQGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPGK

SEQ ID NO: 11
AFQMTQSPSSVSASVGDRVTITCQASESVLNEVSWYQQKPGKAPKLLIYF

ASKLASGVPSRFSGSGSGTDFTLTISSLQPEDFATYYCQQDWSMDNIDNA

FGGGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEVT

HQGLSSPVTKSFNRGEC

Particularly, both SEQ ID NO: 10 and 11 are humanized sequences.

In this specification, "isolated" nucleic acid means a nucleic acid molecule that has been separated from a component of its natural environment. An isolated nucleic acid comprises a nucleic acid molecule typically found in cells comprising a nucleic acid molecule, but the nucleic acid molecule is present extrachromosomally or in a chromosome position different from its natural chromosomal position.

In this specification, "isolated nucleic acid encoding anti-human interleukin-33 monoclonal antibody" means one or more nucleic acid molecules encoding antibody heavy and light chains, including such nucleic acid molecules in a single vector or in separate vectors, as well as such nucleic acid molecules present in one or more positions in host cell.

In this specification, "vector" means a nucleic acid molecule capable of amplifying another nucleic acid to which it has been linked. The term includes a vector that is a self-replicating nucleic acid structure as well as a vector that integrates into the genome of a host cell into which it has been introduced. Certain vectors are capable of guiding the expression of nucleic acids to which they are operably linked. Such vectors are referred to herein as "expression vectors."

In this specification, "host cell", "host cell line" and "host cell culture" are used interchangeably and mean a cell into which exogenous nucleic acid has been introduced, including the progeny of such a cell. Host cells include "transformants" and "transformed cells," which include primary transformed cell and progeny derived therefrom (regardless of passage number). The progeny may not be identical to the parental cell in nucleic acid content, but may comprise mutations. Mutant progeny with the same function or biological activity screened or selected from the originally transformed cells are included in the specification.

In this specification, "pharmaceutical composition" means a product that presents a form in which the biological activity of the active ingredients contained therein can be effectively exerted, and the composition does not comprise any additional components with unacceptable toxicity to the subject to be administered with the formulation.

In this specification, "pharmaceutically acceptable carrier" means an ingredient in a pharmaceutical composition other than an active ingredient, which is nontoxic to a subject. Pharmaceutically acceptable carriers include, but are not limited to, buffers, excipients, stabilizers or preservatives.

In the present application, a "monoclonal antibody" is generally a human antibody, which can be prepared using techniques well known to those skilled in the art, for example, human antibodies are generally described in van Dijk, M. A. and van de Winkel, J. G., Curr. Opin. Pharmacol. 5:368-374 (2001) and Lonberg, N., Curr. Opin. Immunol. 20:450-459 (2008).

Antibodies can be prepared by administering an immunogen to transgenic animals that have been modified to produce intact human antibodies or intact antibodies with human variable regions when stimulated by antigen challenge, these animals typically comprise part or all of the human immunoglobulin loci, which replace endogenous immunoglobulin loci, either present extrachromosomally or integrated randomly in the animal. In such transgenic mice, the endogenous immunoglobulin loci have generally been inactivated. For a review of methods for obtaining human antibodies from transgenic animals, see Lonberg, N., Nat. Biotech. 23:1117-1125 (2005), also see, for example, XENOMOUSE™ technology described in U.S. Pat. Nos. 6,075,181 and 6,150,584; the HUMAB® technology described in U.S. Pat. No. 5,770,429; the K-MMOUSE® technology described in U.S. Pat. No. 7,041,870, and the VELOCIMOUSE® technology described in U.S. Patent Application Publication No. US 2007/0061900. Human variable regions from intact antibodies generated from such animals can be further modified, e.g., by combining with different human constant regions.

Human antibodies can also be prepared by hybridoma-based methods. Human myeloma and mouse-human hybrid myeloma cells have been described for the production of human monoclonal antibodies (see, e.g., Kozbor, D., J. Immunol. 133:3001-3005 (1984); Brodeur, B. R. et al., Monoclonal Antibody Production Techniques and Applications, Marcel Dekker, Inc., New York (1987), pp. 51-63; Boerner, P. et al., J. Immunol. 147:86-95 (1991)). Human antibodies produced via human B-cell hybridoma technology are also described in Li, J. et al., Proc. Natl. Acad. Sci. USA 103:3557-3562 (2006). Other methods include those described, for example, in U.S. Pat. No. 7,189,826 (which describes the generation of monoclonal human IgM antibodies from hybridoma cell lines) and Ni, Xiandai Mianyixue, 26(4); 265-268 (which describes human-human hybridoma). Human hybridoma technology (Trioma technology) is also described in Vollmers, H. P. and Brandlein, S., Histology and Histopathology 20:927-937 (2005); Vollmers, H. P. and Brandlein, S., Methods and Findings in Experimental and Clinical Pharmacology 27: 185-191 (2005).

Human antibodies can also be produced by isolating Fv clone variable domain sequences selected from human-derived phage display libraries, and such variable domain sequences can then be combined with desired human constant domains.

Human antibodies can also be isolated based on the selection of human antibodies from antibody libraries, i.e., by screening for antibodies with one or more activities from the combinatorial libraries. For example, various methods for producing phage display libraries and screening for antibodies with desired binding characteristics from such libraries are known in the art. This approach is reviewed, for example, in Hoogenboom, H. R. et al., Methods in Molecular Biology 178:1-37 (2001), and further described, for example, in McCafferty, J. et al., Nature 348:552-554 (1990); Clackson, T. et al., Nature 352:624-628(1991); Marks, J. D. et al., J. Mol. Biol. 222:581-597(1992); Marks, J. D. and Bradbury, A., Methods in Molecular Biology 248:161-175(2003); Sidhu, S. S. et al., J. Mol. Biol. 338: 299-310 (2004); Lee, C. V. et al., J. Mol. Biol. 340:1073-1093 (2004); Fellouse, F. A., Proc. Natl. Acad. Sci. USA 101:12467-12472 (2004); and Lee, C. V. et al., J. Immunol. Methods 284:119-132 (2004).

In certain phage display methods, repertoires of VH and VL genes are cloned separately by polymerase chain reaction (PCR) and recombined randomly in a phage library, which is then screened for antigen-binding phage in the phage library, as described in Winter, G. et al., Ann. Rev. Immunol. 12:433-455 (1994). Phage typically display antibody fragments as single-chain Fv (scFv) fragments or as Fab fragments. Libraries from immunized sources provide high affinity antibodies to the immunogen without the requirement of constructing hybridomas. Alternatively, the naive repertoire can be cloned (e.g., from a human) to provide a single source of antibodies against a wide range of non-self and also self antigens without any immunization, as described in Griffiths, A. D. et al., EMBO J, 12:725-734 (1993). Finally, naive libraries can also be generated synthetically by cloning unrearranged V gene segments from stem cells and rearranging in vitro using PCR primers containing random sequences to encode the highly variable CDR3 region, as described in Hoogenboom, H. R. and Winter, G., J. Mol. Biol. 227:381-388 (1992). Patent publications describing human antibody phage libraries include, for example: U.S. Pat. No. 5,750,373, and U.S. Patent Publication Nos. 2005/0079574, 2005/0119455, 2005/0266000, 2007/0117126, 2007/0160598, 2007/0237764, 2007/0292936 and 2009/0002360.

The antibody may also be a multispecific antibody, such as a bispecific antibody. Bispecific antibodies are monoclonal antibodies that have binding specificities for at least two different sites. Techniques for making multispecific antibodies include, but are not limited to, recombinant co-expression of two immunoglobulin heavy chain-light chain pairs with different specificities (see Milstein, C. and Cuello, A. C., Nature 305:537-540 (1983); WO 93/08829; and Traunecker, A. et al., EMBO J. 10:3655-3659 (1991)) and "knob-in-hole" engineering (see, e.g., U.S. Pat. No. 5,731,168). It is also possible to generate multispecific antibodies by the following methods: engineering electrostatic manipulation effect for making Fc heterodimer molecules of antibodies (WO 2009/089004); cross linking two or more antibodies or fragments (see e.g. U.S. Pat. No. 4,676,980 and Brennan, M. et al., Science 229:81-83 (1985)); using leucine zippers to make bispecific antibodies (see e.g. Kostelny, S. A. et al., J. Immunol. 148:1547-1553 (1992)); using "diabody" technology for making bispecific antibody fragments (see, e.g., Holliger, P. et al., Proc. Natl. Acad. Sci. USA 90:6444-6448 (1993)); using single chain Fv (scFv) dimers (see, e.g., Gruber, M. et al., J. Immunol. 152:5368-5374 (1994)); and preparing trispecific antibodies (e.g., Tutt, A. et al, J. Immunol. 147:60-69 (1991)).

The monoclonal antibodies described herein also include engineered antibodies having three or more functional antigen binding sites, including "octopus antibodies" (see e.g. US 2006/0025576).

Antibodies herein may also include multispecific antibodies disclosed in WO 2009/080251, WO 2009/080252, WO 2009/080253, WO 2009/080254, WO 2010/112193, WO 2010/115589, WO2010/136172, WO 2010/145792, and WO 2010/145793, WO 2011/117330, WO 2012/025525, WO 2012/025530, WO 2013/026835, WO 2013/026831, WO 2013/164325, or WO 2013/174873.

The monoclonal antibodies described herein may also be antibody variants, e.g., it may be desirable to improve the binding affinity and/or other biological properties of the antibody. Amino acid sequence variants of antibodies can be prepared by introducing appropriate modifications into the nucleotide sequence encoding the antibody, or by peptide synthesis. Such modifications include, for example, deletions, and/or insertions and/or substitutions of residues within the amino acid sequence of the antibody. Any combination of deletions, insertions, and substitutions can be made to obtain the final construct, so long as the final construct possesses the desired characteristics, e.g., antigen binding. Thus, in certain embodiments, provided are antibody variants having one or more amino acid substitutions, sites of interest for substitution mutations include HVR and FR, e.g., amino acid substitutions can be introduced into an antibody of interest and products with desired activity are screened, e.g., retained/improved antigen binding, reduced immunogenicity, or improved ADCC or CDC.

EXAMPLES

Hereinafter, the present application will be described more specifically through examples. It should be understood that the present application is not limited to these examples.

Example 1 Preparation of Anti-Human Interleukin-33 Monoclonal Antibody QX007N

The human interleukin-33 (hIL-33) purchased from Novoprotein Scientific(Shanghai) Inc. was used to immunize New Zealand rabbits. B cell cloning technology was used to obtain antigen-binding specific antibody clones, and then monoclonal antibodies binding to human interleukin-33 and having inhibitory activity against human interleukin-33 were screened out. Firstly, the cell supernatant was detected using Binding ELISA to select clones binding to human interleukin-33; then the clones binding to human interleukin-33 were detected using the HEK Blue™ IL-33 reporter gene cell method, and the clones with inhibitory activity against human interleukin-33 were selected. The above immunization and screening processes were entrusted to commercial companies for completion.

Twelve clones were successively selected for recombinant expression and sequencing. It was determined that 78# had the best cell neutralizing activity, and 78# was humanized. NCBI IgBlast was used to carry out homologous comparison of human IgG germline sequence (Germline), IGHV3-66*01 was selected as the heavy chain CDR transplantation template, and the CDR region of the heavy chain of 78# clone (i.e. CDR-H1 (SEQ ID No: 1), CDR-H2 (SEQ ID No: 2) and CDR-H3 (SEQ ID No: 3)) were grafted into the framework region of IGHV3-66*01; IGKV1-12*01 was selected as the light chain CDR grafting template, and the CDR regions of the light chain of the 78# clone (i.e. CDR-L1 (SEQ ID No: 4), CDR-L2 (SEQ ID No: 5) and CDR-L3 (SEQ ID No: 6)) were transplanted into the framework region of IGKV1-12*01; reverse mutation was performed on the specific site of the framework region to obtain the variable region of the monoclonal antibody QX007N of the present application. Finally, the amino acid sequence of the humanized heavy chain variable region was represented by SEQ ID NO: 7; and the amino acid sequence of the humanized light chain variable region was represented by SEQ ID NO: 8.

The above genes of the heavy chain variable region (SEQ ID NO: 7) and genes of full-length light chain (SEQ ID NO: 11) were obtained by PCR amplification. The heavy chain expression plasmid pQX2.1 was double-digested with HindIII and NheI; the transient expression plasmid pQX1 was double-digested with HindIII and BamHI; the PCR amplified genes were inserted into the corresponding expression plasmid with Infusion recombinase to construct the heavy chain expression plasmid pQX2.1-78VH-Hu25 and light chain expression plasmid pQX2.2-78VK-Hu3. Particularly, pQX2.2 refers to the pQX1 plasmid expressing the light chain.

Figure 1:
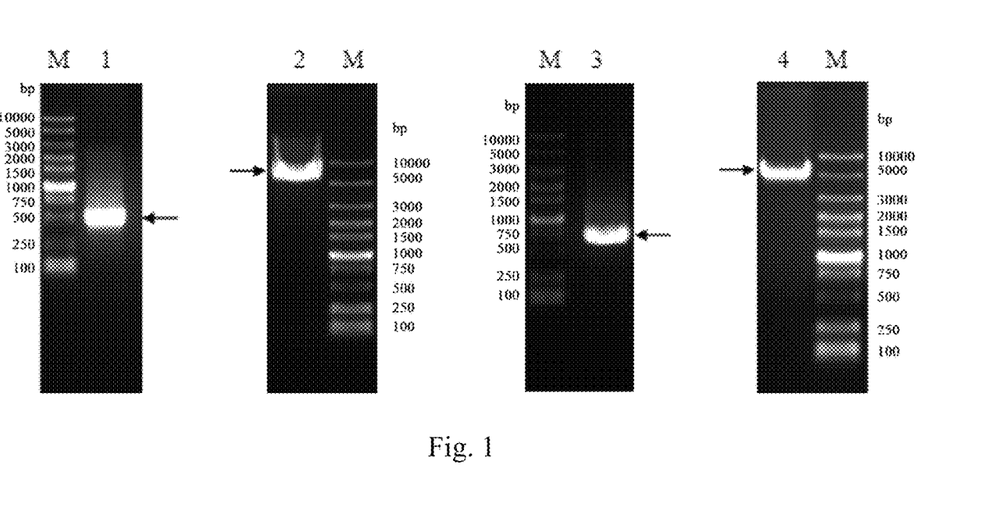
FIG. 1 shows the results of nucleic acid electrophoresis of the constructed QX007N (HZD78-70) transient expression plasmid, wherein M: Marker; Band 1: PCR product 78VH-Hu25; Band 2: pQX2.1, HindIII/NheI; Band 3: PCR product 78VK-Hu3-CK; Band 4: pQX1, HindIII/BamHI.

FIG. 1 shows the results of the double digestion of the plasmid detected by nucleic acid electrophoresis. According to the results in FIG. 1, the PCR amplification results of the heavy chain variable region and the full-length light chain of the antibody and the results of double digestion of the heavy chain and light chain expression plasmids can be seen, wherein both the heavy chain plasmid and the light chain plasmid are about 5000 bp in size, the heavy chain variable region is about 480 bp, and the full-length light chain is about 781 bp.

Figure 2:
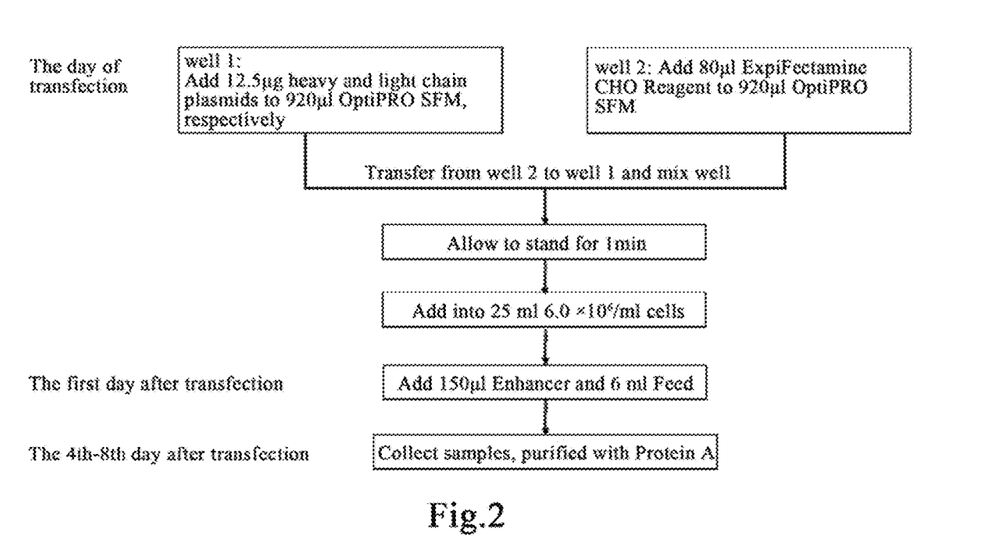
FIG. 2 is a flowchart of transient expression.

The heavy chain expression plasmid pQX2.1-78VH-Hu25 (the full-length amino acid sequence of the heavy chain expressed is represented by SEQ ID NO: 10) and the light chain expression plasmid pQX2.2-78VK-Hu3 (the full-length amino acid sequence of the light chain expressed is represented by SEQ ID NO: 11) with correct sequence were co-transfected into ExpiCHO-S cells. The day before transfection, ExpiCHO-S cells were diluted to $3 \times 10^6$ cells/ml and passaged before transfection. On the day of transfection, the cells were diluted to a cell density of $6 \times 10^6$ cells/ml, and 25 ml cells were placed in a 125 ml shake flask, waiting for transfection. The process of transfection and expression is shown in FIG. 2.

Figure 3:
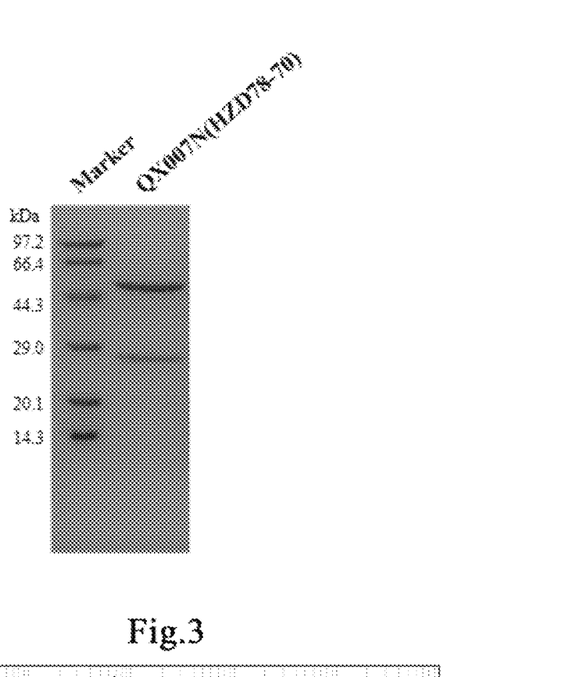
FIG. 3 shows the electrophoretic detection results of QX007N (HZD78-70).

On the $5^{th}$ day after transfection, the culture supernatant was harvested and purified with Protein A in one step. The purified antibody was detected by SDS-PAGE electrophoresis, and named as QX007N (HZD78-70). The result of detecting the antibody by protein electrophoresis is shown in FIG. 3. Protein electrophoresis was detected with denatured reducing gel. The results in FIG. 3 show that there are two bands with sizes of about 50 kDa and 25 kDa respectively, consistent with the theoretical molecular weight of the heavy chain (49.3 kDa) and light chain (23.4 kDa).

Example 2 Determination of Equilibrium Dissociation Constant ($K_D$)

Biacore T200 was used to detect the affinity of QX007N (HZD78-70) binding to human interleukin-33, and all processes were carried out at 25° C. Commercialized Protein A chip was used to immobilize an appropriate amount of antibody by capture method, so that the Rmax was about 50 RU, and the capture flow rate was 10 μl/min. The antigen was diluted by gradient, the flow rate of the instrument was switched to 30 μl/min, and the antigen flowed through the reference channel and the channel of the immobilized antibody in order of concentration from low to high, and the buffer was used as a negative control. After each binding and dissociation, the chip was regenerated with glycine at pH 1.5. The 1:1 binding model in Kinetics option was selected for fitting using the analysis software that comes with the instrument, and the binding rate constant $k_a$, the dissociation rate constant $k_d$ and the equilibrium dissociation constant $K_D$ value of the antibody were calculated.

In addition, the affinity of QX007N (HZD78-70) and Etokimab/ANB020, a monoclonal antibody against human interleukin-33 developed by AnaptysBio were compared, and the detection method for known antibodies was the same as that for QX007N. The results are shown in Table 1. Particularly, Etokimab/ANB020 was self-made by constructing an expression plasmid according to the APE4909 sequence provided by the patent WO2015106080A2, and transiently transfecting ExpiCHO-S cells.

TABLE 1

Affinity of anti-human interleukin-33 antibodies binding to human interleukin-33

| Sample name | $k_a$ ($10^5$ $M^{-1}S^{-1}$) | $k_d$ ($10^{-4}$ $S^{-1}$) | $K_D$ ($10^{-10}$M) |
|---|---|---|---|
| QX007N | 3.92 | 4.81 | 12.28 |
| ANB 020 | 4.24 | 3.69 | 8.69 |

In addition, based on the same detection method as above, we also found that Etokimab/ANB020 can bind to interleukin-33 in cynomolgus monkeys and rhesus monkeys, while QX007N (HZD78-70) can bind to interleukin-33 in cynomolgus monkeys, but not rhesus monkeys.

Example 3 Detection of the Activity of Neutralizing NF-κB/AP-1 Signal Transduction in HEK Blue™ IL-33 Cells Induced by Human Interleukin-33

HEK Blue™ IL-33 cells were generated by stably transfecting human embryonic kidney cells HEK 293 with human IL1RL1 gene, and the responses of TNF-α and IL-1β were blocked, so HEK Blue™ IL-33 cells specifically respond to IL-33. The binding of interleukin-33 to IL-1RL1/IL-1RAcP on the cell surface triggered a signal cascade reaction, leading to NF-κB/AP-1 signal transduction and production of secreted alkaline phosphatase (SEAP), according to which the biological activity of interleukin-33 can be detected or antibody screening can be carried out.

The neutralizing activity of QX007N (HZD78-70) against human interleukin-33 was detected using HEK Blue™ IL-33 cells. HEK Blue™ IL-33 cells were plated into 96 wells with $4 \times 10^4$ cells per well and cultured overnight at 37° C. and 5% $CO_2$; the antibody was diluted to a concentration range of 0 to 500 ng/ml, and the diluent was mixed with 2 ng/ml of recombinant human interleukin-33 and incubated for 1 hour for 24 hours; after incubation, it was added to the cells and cultured at 37° C. and 5% $CO_2$ conditions; the cell culture supernatant was collected and added to the QUANTI Blue™ detection reagent (InvivoGen, rep qbs2) at a ratio of 1:10, and then reacting at 37° C. for 1 hour. The $OD_{630nm}$ value was detected using a Varioskan LUX multifunctional microplate reader, and the data were analyzed using SoftMax Pro software with a 4-parameter curve fitting analysis (FIG. 4), so as to analyze the antagonistic activity of the antibody.

Figure 4:
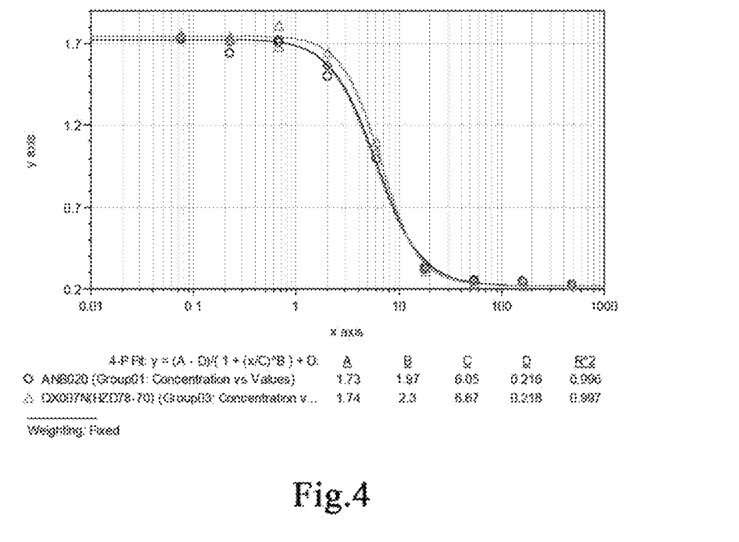
FIG. 4 shows the activities of QX007N(HZD78-70) and Etokimab/ANB020 neutralizing NF-κB/AP-1 signal transduction in HEK Blue™ IL-33 cells induced by recombinant human interleukin-33.

The results in FIG. 4 shows that: QX007N (HZD78-70) can inhibit NF-κB/AP-1 signal transduction in HEK Blue™ IL-33 cells induced by recombinant human interleukin-33, with an $IC_{50}$ of 6.67 ng/ml; in contrast, for Etokimab/ANB020, the $IC_{50}$ measured by the same method is 6.05 ng/ml.

Example 4 Detection of the Activity of Neutralizing NF-κB/AP-1 Signal Transduction in HEK Blue™ IL-33 Cells Induced by Natural Human Interleukin-33

Natural human interleukin-33 was prepared and the neutralizing activity of QX007N (HZD78-70) against natural human interleukin-33 was verified. HFL-1 cells were cultured and induced with 200 ng/ml TNF-α to culture for 24 hours, cells were collected and lysed using repeated freeze-thaw method. The supernatant of the cell lysate which contains human interleukin-33 was collected, its activity was verified by HEK Blue™ IL-33 cells.

HEK Blue™ IL-33 cells were plated into 96 wells with $4 \times 10^4$ cells per well and cultured overnight at 37° C. and 5% $CO_2$; after the antibody was diluted to a concentration range of 0 to 1000 ng/ml, the diluent and natural human interleukin-33 were added, mixed well and added to the cells, and cultured at 37° C. and 5% $CO_2$ for 24 hours, then the cell culture supernatant was collected and added to QUANTI-Blue™ detection reagent at a ratio of 1:10, and then reacting at 37° C. for 1 hour. The $OD_{630nm}$ value was detected using a Varioskan LUX multifunctional microplate reader, and the data were analyzed using SoftMax Pro software with a 4-parameter curve fitting analysis (FIG. 5), so as to analyze the neutralizing activity of the antibody.

Figure 5:
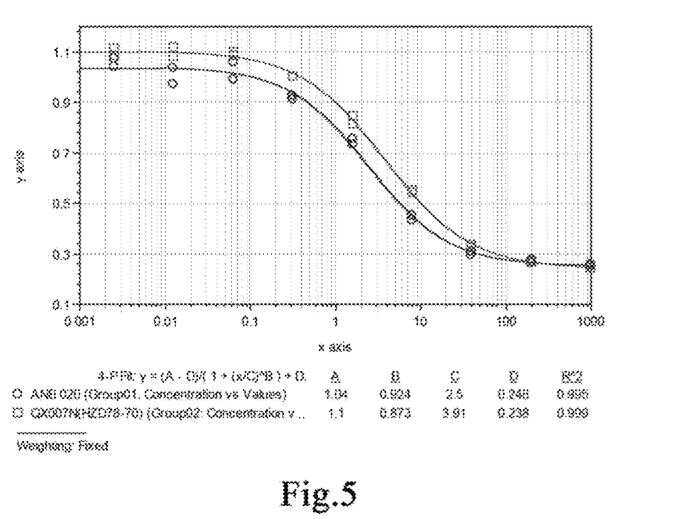
FIG. 5 shows the activities of QX007N(HZD78-70) and Etokimab/ANB020 neutralizing NF-κB/AP-1 signal transduction in HEK Blue™ IL-33 cells induced by natural human interleukin-33.

The results in FIG. 5 shows that: QX007N (HZD78-70) can inhibit NF-κB/AP-1 signal transduction in HEK Blue™ IL-33 cells induced by natural human interleukin-33, with an $IC_{50}$ of 3.91 ng/ml; in contrast, for Etokimab/ANB020, the $IC_{50}$ measured by the same method is 2.5 ng/ml.

Example 5 Detection of the Activity of Neutralizing the Release of IL-5 from KU812 (Human Peripheral Blood Eosinophilic Leukemia Cells) Induced by Human Interleukin-33

Taking the release of IL-5 from KU812 (human peripheral blood basophilic leukemia cells) induced by human interleukin-33 as an index, the activity of QX007N (HZD78-70) in neutralizing human interleukin-33 was evaluated. KU812 cells were inoculated into a 96 well plate ($2 \times 10^5$ cells/well), subsequently, antibodies and recombinant human interleukin-33 (final concentration 4 ng/ml) were added and cultured at 37° C. and 5% $CO_2$ for 24 hours, then the cell culture supernatant was collected and the expression of IL-5 in the supernatant was detected using Human IL-5 DuoSet ELISA (R&D, DY205). The $OD_{450nm}$ value was detected using a Varioskan LUX multifunctional microplate reader, and the data were analyzed using SoftMax Pro software with a 4-parameter curve fitting analysis (FIG. 6), so as to analyze the neutralizing activity of the antibody.

Figure 6:
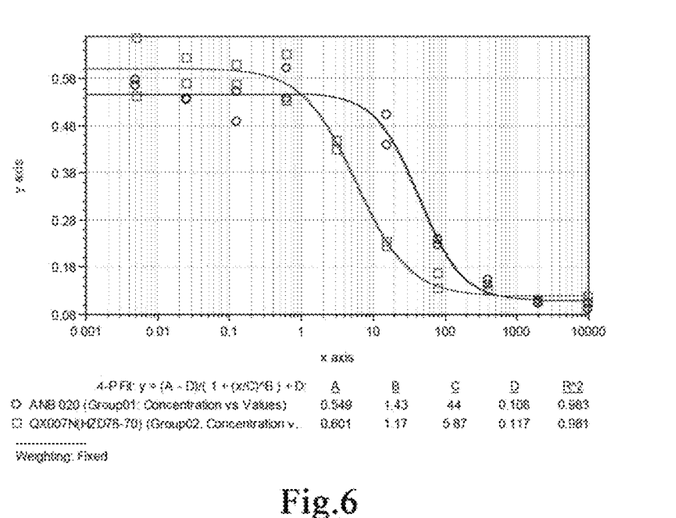
FIG. 6 shows the activities of QX007N(HZD78-70) and Etokimab/ANB020 neutralizing the release of IL-5 from KU812 cells induced by recombinant human interleukin-33.

The results in FIG. 6 shows that: QX007N (HZD78-70) can neutralize the activity of releasing IL-5 from KU812 (human peripheral blood eosinophilic leukemia cells) induced by human interleukin-33, with an $IC_{50}$ of 5.87 ng/ml; in contrast, for Etokimab/ANB020, the $IC_{50}$ measured by the same method is 44 ng/ml.

Example 6 Detection of the Activity of Neutralizing the Release of IFN-γ from Human Whole Blood Induced by Human Interleukin-33

The neutralizing activity of QX007N(HZD78-70) was further characterized with monocytes in human whole blood as the measurement basis and IFN-γ as the measurement index. Whole blood from healthy volunteers was plated (100 μL/well), then antibody and recombinant human interleukin-33 (final concentration 4 ng/ml) were added and cultured at 37° C. and 5% $CO_2$ for 24 hours. The $OD_{450nm}$ value was detected using a Varioskan LUX multifunctional microplate reader, and the data were analyzed using SoftMax Pro software with a 4-parameter curve fitting analysis (FIG. 7), so as to analyze the neutralizing activity of the antibody.

Figure 7:
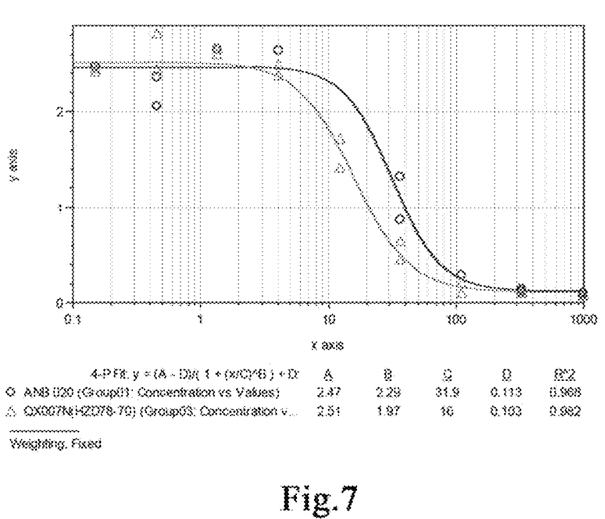
FIG. 7 shows the activities of QX007N(HZD78-70) and Etokimab/ANB020 neutralizing the release of IFN-γ from human whole blood induced by recombinant human interleukin-33.

The results in FIG. 7 shows that: QX007N (HZD78-70) can neutralize the activity of releasing IFN-γ from human whole blood induced by human interleukin-33, with an $IC_{50}$ of 16 ng/ml; in contrast, for Etokimab/ANB020, the $IC_{50}$ measured by the same method is 31.9 ng/ml.

The invention claimed is:

1. An isolated anti-human interleukin-33 monoclonal antibody, comprising three heavy chain complementarity determining regions and three light chain complementarity determining regions, the three heavy chain complementarity determining regions are CDR-H1, CDR-H2 and CDR-H3, and the three light chain complementarity determining regions are CDR-L1, CDR-L2 and CDR-L3, wherein:

the amino acid sequence of CDR-H1 is represented by SEQ ID NO: 1;

the amino acid sequence of CDR-H2 is represented by SEQ ID NO: 2;

the amino acid sequence of CDR-H3 is represented by SEQ ID NO: 3;

the amino acid sequence of CDR-L1 is represented by SEQ ID NO: 4;

the amino acid sequence of CDR-L2 is represented by SEQ ID NO: 5; and the amino acid sequence of CDR-L3 is represented by SEQ ID NO: 6.

2. The monoclonal antibody according to claim 1, which comprises a heavy chain variable region and a light chain variable region, wherein the amino acid sequence of the heavy chain variable region is represented by SEQ ID NO: 7; and the amino acid sequence of the light chain variable region is represented by SEQ ID NO: 8.

3. An isolated nucleic acid encoding the monoclonal antibody of claim 1.

4. A host cell comprising an expression vector, wherein the expression vector comprises the nucleic acid of claim 3.

5. A method for producing a monoclonal antibody, which comprises;

(i) culturing the host cell of claim 4 to produce the monoclonal antibody, and (ii) Isolating the antibody;

wherein the monoclonal antibody is an isolated anti-human interleukin-33 monoclonal antibody, comprising three heavy chain complementarity determining regions and three light chain complementarity determining regions, the three heavy chain complementarity determining regions are CDR-H1, CDR-H2 and CDR-H3, and the three light chain complementarity determining regions are CDR-L1, CDR-L2 and CDR-L3, wherein:

the amino acid sequence of CDR-H1 is represented by SEQ ID NO: 1;

the amino acid sequence of CDR-H2 is represented by SEQ ID NO: 2;

the amino acid sequence of CDR-H3 is represented by SEQ ID NO: 3;

the amino acid sequence of CDR-L1 is represented by SEQ ID NO: 4;

the amino acid sequence of CDR-L2 is represented by SEQ ID NO: 5; and the amino acid sequence of CDR-L3 is represented by SEQ ID NO: 6.

6. A pharmaceutical composition, which comprises the monoclonal antibody of claim 1 and a pharmaceutically acceptable carrier.

7. A method for treating a disease related to human interleukin-33-mediated signal transduction, which comprises administering the monoclonal antibody of claim 1 or a pharmaceutical composition comprising said monoclonal antibody and a pharmaceutically acceptable carrier to a subject in need thereof; wherein the disease related to human interleukin-33-mediated signal transduction is any one or two or more diseases selected from the group consisting of: asthma, chronic obstructive pulmonary disease, chronic sinusitis, and atopic dermatitis;

wherein the activity of IL-33 is neutralized following administration to the subject.

* * * * *

```
                        SEQUENCE LISTING

Sequence total quantity: 11
SEQ ID NO: 1            moltype = AA  length = 5
FEATURE                 Location/Qualifiers
REGION                  1..5
                        note = synthetic
source                  1..5
                        mol_type = protein
                        organism = synthetic construct
SEQUENCE: 1
SYHMI                                                                    5

SEQ ID NO: 2            moltype = AA  length = 16
FEATURE                 Location/Qualifiers
REGION                  1..16
                        note = synthetic
source                  1..16
                        mol_type = protein
                        organism = synthetic construct
SEQUENCE: 2
VIYPNSNIYY ATWAKG                                                       16

SEQ ID NO: 3            moltype = AA  length = 12
FEATURE                 Location/Qualifiers
REGION                  1..12
                        note = synthetic
source                  1..12
                        mol_type = protein
                        organism = synthetic construct
SEQUENCE: 3
TIYVHVYSAL SI                                                           12

SEQ ID NO: 4            moltype = AA  length = 11
FEATURE                 Location/Qualifiers
REGION                  1..11
                        note = synthetic
source                  1..11
                        mol_type = protein
                        organism = synthetic construct
SEQUENCE: 4
QASESVLNEV S                                                            11

SEQ ID NO: 5            moltype = AA  length = 7
FEATURE                 Location/Qualifiers
REGION                  1..7
                        note = synthetic
source                  1..7
                        mol_type = protein
                        organism = synthetic construct
SEQUENCE: 5
FASKLAS                                                                  7

SEQ ID NO: 6            moltype = AA  length = 12
FEATURE                 Location/Qualifiers
REGION                  1..12
                        note = synthetic
source                  1..12
                        mol_type = protein
```

```
                        organism = synthetic construct
SEQUENCE: 6
QQDWSMDNID NA                                                          12

SEQ ID NO: 7            moltype = AA  length = 120
FEATURE                 Location/Qualifiers
REGION                  1..120
                        note = synthetic
source                  1..120
                        mol_type = protein
                        organism = synthetic construct
SEQUENCE: 7
EVQLVESGGG LVQPGGSLRL SCAASGFSLS SYHMIWVRQA PGKGLEWVGV IYPNSNIYYA      60
TWAKGRFTIS RDNSKNTLYL QMNSLRAEDT AVYYCARTIY VHVYSALSIW GQGTLVTVSS     120

SEQ ID NO: 8            moltype = AA  length = 110
FEATURE                 Location/Qualifiers
REGION                  1..110
                        note = synthetic
source                  1..110
                        mol_type = protein
                        organism = synthetic construct
SEQUENCE: 8
AFQMTQSPSS VSASVGDRVT ITCQASESVL NEVSWYQQKP GKAPKLLIYF ASKLASGVPS      60
RFSGSGSGTD FTLTISSLQP EDFATYYCQQ DWSMDNIDNA FGGGTKVEIK                110

SEQ ID NO: 9            moltype = AA  length = 159
FEATURE                 Location/Qualifiers
REGION                  1..159
                        note = synthetic
source                  1..159
                        mol_type = protein
                        organism = synthetic construct
SEQUENCE: 9
SITGISPITE YLASLSTYND QSITFALEDE SYEIYVEDLK KDEKKDKVLL SYYESQHPSN      60
ESGDGVDGKM LMVTLSPTKD FWLHANNKEH SVELHKCEKP LPDQAFFVLH NMHSNCVSFE    120
CKTDPGVFIG VKDNHLALIK VDSSENLCTE NILFKLSET                           159

SEQ ID NO: 10           moltype = AA  length = 450
FEATURE                 Location/Qualifiers
REGION                  1..450
                        note = synthetic
source                  1..450
                        mol_type = protein
                        organism = synthetic construct
SEQUENCE: 10
EVQLVESGGG LVQPGGSLRL SCAASGFSLS SYHMIWVRQA PGKGLEWVGV IYPNSNIYYA      60
TWAKGRFTIS RDNSKNTLYL QMNSLRAEDT AVYYCARTIY VHVYSALSIW GQGTLVTVSS     120
ASTKGPSVFP LAPSSKSTSG GTAALGCLVK DYFPEPVTVS WNSGALTSGV HTFPAVLQSS     180
GLYSLSSVVT VPSSSLGTQT YICNVNHKPS NTKVDKKVEP KSCDKTHTCP PCPAPELLGG     240
PSVFLFPPKP KDTLMISRTP EVTCVVVDVS HEDPEVKFNW YVDGVEVHNA KTKPREEQYN     300
STYRVVSVLT VLHQDWLNGK EYKCKVSNKA LPAPIEKTIS KAKGQPREPQ VYTLPPSRDE     360
LTKNQVSLTC LVKGFYPSDI AVEWESNGQP ENNYKTTPPV LDSDGSFFLY SKLTVDKSRW     420
QQGNVFSCSV MHEALHNHYT QKSLSLSPGK                                     450

SEQ ID NO: 11           moltype = AA  length = 217
FEATURE                 Location/Qualifiers
REGION                  1..217
                        note = synthetic
source                  1..217
                        mol_type = protein
                        organism = synthetic construct
SEQUENCE: 11
AFQMTQSPSS VSASVGDRVT ITCQASESVL NEVSWYQQKP GKAPKLLIYF ASKLASGVPS      60
RFSGSGSGTD FTLTISSLQP EDFATYYCQQ DWSMDNIDNA FGGGTKVEIK RTVAAPSVFI    120
FPPSDEQLKS GTASVVCLLN NFYPREAKVQ WKVDNALQSG NSQESVTEQD SKDSTYSLSS     180
TLTLSKADYE KHKVYACEVT HQGLSSPVTK SFNRGEC                             217
```